(12) United States Patent
Rizoiu et al.

(10) Patent No.: US 7,696,466 B2
(45) Date of Patent: *Apr. 13, 2010

(54) ELECTROMAGNETIC ENERGY DISTRIBUTIONS FOR ELECTROMAGNETICALLY INDUCED MECHANICAL CUTTING

(75) Inventors: Ioana M. Rizoiu, Dana Point, CA (US); Andrew I. Kimmel, San Clemente, CA (US)

(73) Assignee: Biolase Technology, Inc., Irvine, CA (US)

(*) Notice: Subject to any disclaimer, the term of this patent is extended or adjusted under 35 U.S.C. 154(b) by 377 days.

This patent is subject to a terminal disclaimer.

(21) Appl. No.: 11/523,492

(22) Filed: Sep. 18, 2006

(65) Prior Publication Data

US 2007/0014322 A1     Jan. 18, 2007

Related U.S. Application Data

(63) Continuation of application No. 10/993,498, filed on Nov. 18, 2004, now Pat. No. 7,108,693, which is a continuation of application No. 10/164,451, filed on Jun. 6, 2002, now Pat. No. 6,821,272, which is a continuation of application No. 09/883,607, filed on Jun. 18, 2001, now abandoned, which is a continuation of application No. 08/903,187, filed on Jun. 12, 1997, now Pat. No. 6,288,499, which is a continuation-in-part of application No. 08/522,503, filed on Aug. 31, 1995, now Pat. No. 5,741,247.

(51) Int. Cl.
    *H01J 31/50*  (2006.01)
(52) U.S. Cl. ............................ 250/214 VT; 250/339.01; 606/3; 315/200 A

(58) Field of Classification Search .................. 606/15, 606/128, 2, 3, 10; 372/38.02, 23, 69, 70; 315/200 A, 241 P, 241 S, 291, 307; 250/214 VT, 250/339.01, 339.06, 431, 526
See application file for complete search history.

(56) References Cited

U.S. PATENT DOCUMENTS 3,679,863 A     7/1972   Houldcroft et al.

(Continued)

FOREIGN PATENT DOCUMENTS

DE          4138468          3/1993

(Continued)

OTHER PUBLICATIONS

International Search Report & Written Opinion, Sep. 2, 2005, PCT/US05/00849.

(Continued)

*Primary Examiner*—Douglas W Owens
*Assistant Examiner*—Jimmy T Vu
(74) *Attorney, Agent, or Firm*—Stout, Uxa, Buyan & Mullins, LLP

(57) ABSTRACT

Output optical energy pulses including relatively high energy magnitudes at the beginning of each pulse are disclosed. As a result of the relatively high energy magnitudes which lead each pulse, the leading edge of each pulse includes a relatively large slope. This slope is preferably greater than or equal to 5. Additionally, the full-width half-max value of the output optical energy distributions are between 0.025 and 250 microseconds and, more preferably, are about 70 microseconds. A flashlamp is used to drive the laser system, and a current is used to drive the flashlamp. A flashlamp current generating circuit includes a solid core inductor which has an inductance of 50 microhenries and a capacitor which has a capacitance of 50 microfarads.

16 Claims, 3 Drawing Sheets

U.S. PATENT DOCUMENTS

| | | | |
|---|---|---|---|
| 3,679,998 A | 7/1972 | Dahlinger | |
| 3,914,648 A | 10/1975 | Friedman et al. | |
| 3,991,296 A | 11/1976 | Kojima et al. | |
| 4,005,333 A | 1/1977 | Nichols | |
| 4,276,518 A | 6/1981 | Ferguson | |
| 4,445,892 A | 5/1984 | Hussein | |
| 4,550,275 A | 10/1985 | O'Loughlin | |
| 4,724,299 A | 2/1988 | Hammeke | |
| 4,826,431 A | 5/1989 | Fujimura et al. | |
| 4,862,888 A | 9/1989 | Yessik | |
| 4,908,030 A | 3/1990 | Linkow et al. | |
| 4,910,438 A | 3/1990 | Farnsworth | |
| 4,913,142 A | 4/1990 | Kittrell et al. | |
| 4,931,047 A | 6/1990 | Broadwin et al. | |
| 4,985,027 A | 1/1991 | Dressel | |
| 5,086,378 A | 2/1992 | Prince | |
| 5,092,773 A | 3/1992 | Levy | |
| 5,092,864 A * | 3/1992 | Hayes et al. | 606/10 |
| 5,102,410 A | 4/1992 | Dressel | |
| 5,151,029 A | 9/1992 | Levy | |
| 5,196,004 A | 3/1993 | Sinofsky | |
| 5,199,870 A * | 4/1993 | Steiner et al. | 433/29 |
| 5,221,561 A | 6/1993 | Flicstein et al. | |
| 5,237,331 A * | 8/1993 | Henderson et al. | 342/54 |
| 5,242,454 A | 9/1993 | Gundlach et al. | |
| 5,263,950 A | 11/1993 | L'Esperance, Jr. | |
| 5,267,856 A | 12/1993 | Wolbarsht et al. | |
| 5,313,481 A | 5/1994 | Cook et al. | |
| 5,318,562 A * | 6/1994 | Levy et al. | 606/16 |
| 5,334,019 A | 8/1994 | Goldsmith et al. | |
| 5,374,266 A | 12/1994 | Kataoka et al. | |
| 5,389,988 A | 2/1995 | Daitoku | |
| 5,401,171 A | 3/1995 | Paghdiwala | |
| 5,409,376 A | 4/1995 | Murphy | |
| 5,552,675 A | 9/1996 | Lemelson | |
| 5,554,172 A | 9/1996 | Horner et al. | |
| 5,694,046 A | 12/1997 | Hillerich et al. | |
| 5,723,864 A | 3/1998 | Atkinson et al. | |
| 5,729,562 A | 3/1998 | Birx et al. | |
| 5,741,247 A * | 4/1998 | Rizoiu et al. | 606/10 |
| 5,755,751 A | 5/1998 | Eckhouse | |
| 5,764,672 A | 6/1998 | Ukita et al. | |
| 5,785,521 A | 7/1998 | Rizoiu et al. | |
| 5,820,627 A * | 10/1998 | Rosen et al. | 606/15 |
| 5,825,958 A | 10/1998 | Gollihar et al. | |
| 5,828,803 A | 10/1998 | Eckhouse | |
| 5,869,805 A | 2/1999 | Beyer et al. | |
| 6,080,148 A | 6/2000 | Damasco et al. | |
| 6,083,218 A | 7/2000 | Chou | |
| 6,106,516 A | 8/2000 | Massengill | |
| 6,118,521 A | 9/2000 | Jung et al. | |
| 6,223,987 B1 | 5/2001 | Knowles et al. | |
| 6,231,567 B1 | 5/2001 | Rizoiu et al. | |
| 6,254,597 B1 | 7/2001 | Rizoiu et al. | |
| 6,288,499 B1 | 9/2001 | Rizoiu et al. | |
| 6,315,772 B1 | 11/2001 | Marchitto et al. | |
| 6,350,123 B1 | 2/2002 | Rizoiu et al. | |
| 6,389,193 B1 | 5/2002 | Kimmel et al. | |
| 6,449,301 B1 | 9/2002 | Wu et al. | |
| 6,561,803 B1 | 5/2003 | Rizoiu et al. | |
| 6,669,685 B1 | 12/2003 | Rizoiu et al. | |
| 6,878,899 B2 * | 4/2005 | Smart | 219/121.61 |
| 6,902,290 B2 | 6/2005 | Watts et al. | |
| 7,108,693 B2 * | 9/2006 | Rizoiu et al. | 606/15 |
| 2002/0149324 A1 | 10/2002 | Rizoiu et al. | |
| 2005/0137655 A1 | 6/2005 | MacFarland | |
| 2005/0143792 A1 | 6/2005 | Jay | |

FOREIGN PATENT DOCUMENTS

| | | |
|---|---|---|
| EP | 0181199 | 5/1986 |
| EP | 0192833 | 9/1986 |
| EP | 0454312 A2 | 10/1991 |
| EP | 0454312 A3 | 10/1991 |
| GB | 2 023 330 | 12/1979 |
| GB | 2297610 A | 8/1996 |
| JP | 5945092 | 3/1984 |
| JP | 200301465 | 1/2003 |
| WO | 96 41657 | 12/1996 |
| WO | 97 07928 A3 | 3/1997 |
| WO | 9707928 A2 | 3/1997 |
| WO | 97 45165 | 12/1997 |
| WO | 98/57526 A | 12/1998 |

OTHER PUBLICATIONS

International Search Report & Written Opinion, Jul. 31, 2006, PCT/US06/00989.
International Search Report & Written Opinion, Oct. 25, 2006, PCT/US05/28891.
International Search Report, Dec. 10, 1998, PCT/US98/12357.
Written Opinion, Apr. 15, 1999, PCT/US98/12357.
European Search Report, Jun. 6, 2005, EP 05 07 5231.
Partial European Search Report, Apr. 6, 2000, EP 98 92 9060.
T.S. Fahlen, Efficient Quarter-Joule KrF Laser with Corona Preionization, IEEE Journal of Quantum Electronics, vol. QE-15, No. 5, pp. 311-312. May 5, 1979.
Bernard Grob, Basic Electronics, Glencoe division of Macmillan/McGraw-Hill, pp. 690-681. 1989.
New Laser—Matter Interaction Concept to Enhance Tissue Cutting Efficiency by Ioana M. Rizoiu and Larry G. DeShazer, published in SPIE Col. 2134A Laser-Tissue Interaction V(1994)/309.
International Search Report, Jun. 30, 2008, PCT/US08/051963.
International Search Report, May 23, 2008, PCT/US08/051967.
Supplemental European Search Report, Apr. 25, 2008 from EP05705483.

\* cited by examiner

ELECTROMAGNETIC ENERGY DISTRIBUTIONS FOR ELECTROMAGNETICALLY INDUCED MECHANICAL CUTTING

This application is a continuation of U.S. application Ser. No. 10/993,498, now U.S. Pat. No. 7,108,693, filed Nov. 18, 2004 and entitled ELECTROMAGNETIC ENERGY DISTRIBUTIONS FOR ELECTROMAGNETICALLY INDUCED MECHANICAL CUTTING. U.S. application Ser. No. 10/993,498 is a continuation of U.S. application Ser. No. 10/164,451, filed Jun. 6, 2002, now U.S. Pat. No. 6,821,272, which is a continuation of U.S. application Ser. No. 09/883,607 filed Jun. 18, 2001, now abandoned, which is a continuation of U.S. application Ser. No. 08/903,187, filed Jun. 12, 1997, now U.S. Pat. No. 6,288,499, which is a continuation-in-part of U.S. application Ser. No. 08/522,503, now U.S. Pat. No. 5,741,247, filed Aug. 31, 1995 and entitled ATOMIZED FLUID PARTICLES FOR ELECTROMAGNETICALLY INDUCED CUTTING, which is commonly assigned and the contents of which are expressly incorporated herein by reference.

BACKGROUND OF THE INVENTION

1. Field of the Invention

The present invention relates generally to lasers and, more particularly, to output optical energy distributions of lasers.

2. Description of Related Art

A variety of laser systems are present in the prior art. A solid-state laser system generally comprises a laser rod for emitting coherent light and a stimulation source for stimulating the laser rod to emit the coherent light. Flashlamps are typically used as stimulation sources for Erbium laser systems, for example. The flashlamp is driven by a flashlamp current, which comprises a predetermined pulse shape and a predetermined frequency.

The flashlamp current drives the flashlamp at the predetermined frequency, to thereby produce an output flashlamp light distribution having substantially the same frequency as the flashlamp current. This output flashlamp light distribution from the flashlamp drives the laser rod to produce coherent light at substantially the same predetermined frequency as the flashlamp current. The coherent light generated by the laser rod has an output optical energy distribution over time that generally corresponds to the pulse shape of the flashlamp current.

The pulse shape of the output optical energy distribution over time typically comprises a relatively gradually rising energy that ramps up to a maximum energy, and a subsequent decreasing energy over time. The pulse shape of a typical output optical energy distribution can provide a relatively efficient operation of the laser system, which corresponds to a relatively high ratio of average output optical energy to average power inputted into the laser system.

The prior art pulse shape and frequency may be suitable for thermal cutting procedures, for example, where the output optical energy is directed onto a target surface to induce cutting. New cutting procedures, however, do not altogether rely on laser-induced thermal cutting mechanisms. More particularly, a new cutting mechanism directs output optical energy from a laser system into a distribution of atomized fluid particles located in a volume of space just above the target surface. The output optical energy interacts with the atomized fluid particles causing the atomized fluid particles to expand and impart electromagnetically-induced mechanical cutting forces onto the target surface. As a result of the unique interactions of the output optical energy with the atomized fluid particles, typical prior art output optical energy distribution pulse shapes and frequencies have not been especially suited for providing optical electromagnetically-induced mechanical cutting. Specialized output optical energy distributions are required for optimal cutting when the output optical energy is directed into a distribution of atomized fluid particles for effectuating electromagnetically-induced mechanical cutting of the target surface.

SUMMARY OF THE INVENTION

The output optical energy distributions of the present invention comprise relatively high energy magnitudes at the beginning of each pulse. As a result of these relatively high energy magnitudes at the beginning of each pulse, the leading edge of each pulse comprises a relatively large slope. This slope is preferably greater than or equal to 5. Additionally, the full-width half-max (FWHM) values of the output optical energy distributions are greater than 0.025 microseconds. More preferably, the full-width half-max values are between 0.025 and 250 microseconds and, more preferably, are between 10 and 150 microseconds. The full-width half-max value is about 70 microseconds in the illustrated embodiment. A flashlamp is used to drive the laser system, and a current is used to drive the flashlamp. A flashlamp current generating circuit comprises a solid core inductor having an inductance of about 50 microhenries and a capacitor having a capacitance of about 50 microfarads.

The present invention, together with additional features and advantages thereof, may best be understood by reference to the following description taken in connection with the accompanying illustrative drawings.

DETAILED DESCRIPTION OF THE PRESENTLY PREFERRED EMBODIMENTS

Figure 1:
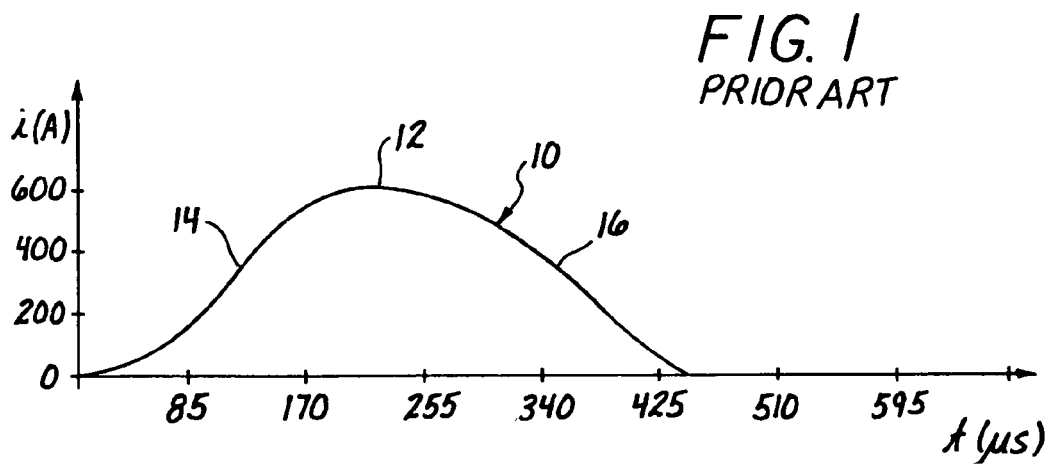
FIG. 1 is a plot of flashlamp-driving current versus time according to the prior art.

Referring more particularly to the drawings, FIG. 1 illustrates a plot of flashlamp-driving current versus time according to the prior art. The flashlamp-driving current 10 initially ramps up to a maximum value 12. The initial ramp 14 typically comprises a slope (current divided by time) of between 1 and 4. After reaching the maximum value 12, the flashlamp-driving current 10 declines with time, as illustrated by the declining current portion 16. The prior art flashlamp-driving current 10 may typically comprise a frequency or repetition rate of 1 to 15 hertz (Hz). Additionally, the flashlamp-driving current 10 of the prior art may typically comprise a pulse width greater than 300 microseconds. The full-width half-max value of the flashlamp-driving current 10 is typically between 250 and 300 microseconds. The full-width half-max value is defined as a value of time corresponding to a length of the full-width half-max range plotted on the time axis. The full-width half-max range is defined on the time axis from a beginning time, where the amplitude first reaches one half of the peak amplitude of the entire pulse, to an ending time, where the amplitude reaches one half of the peak amplitude a final time within the pulse. The full-width half-max value is the difference between the beginning time and the ending time.

Figure 2:
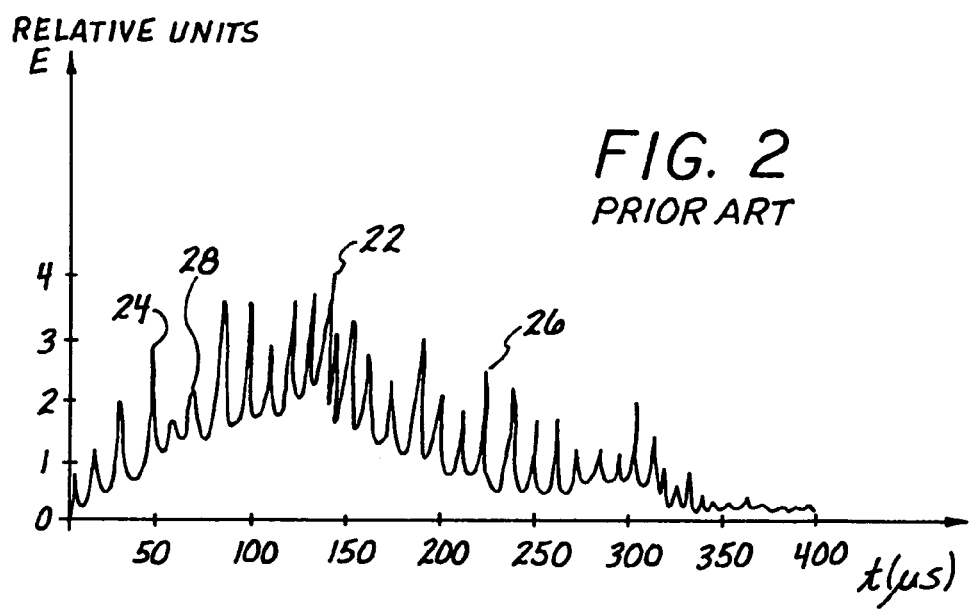
FIG. 2 is a plot of output optical energy versus time for a laser system according to the prior art.

FIG. 2 illustrates a plot of energy versus time for the output optical energy of a typical prior art laser. The output optical energy distribution 20 generally comprises a maximum value 22, an initial ramp 24, and a declining output energy portion 26. The micropulses 28 correspond to population inversions within the laser rod as coherent light is generated by stimulated emission. The average power of the laser can be defined as the power delivered over a predetermined period of time, which typically comprises a number of pulses. The efficiency of the laser system can be defined as a ratio of the output optical power of the laser, to the input power into the system that is required to drive the flashlamp. Typical prior art laser systems are designed with flashlamp-driving currents 10 and output optical energy distributions 20 which optimize the efficiency of the system.

Figure 3:
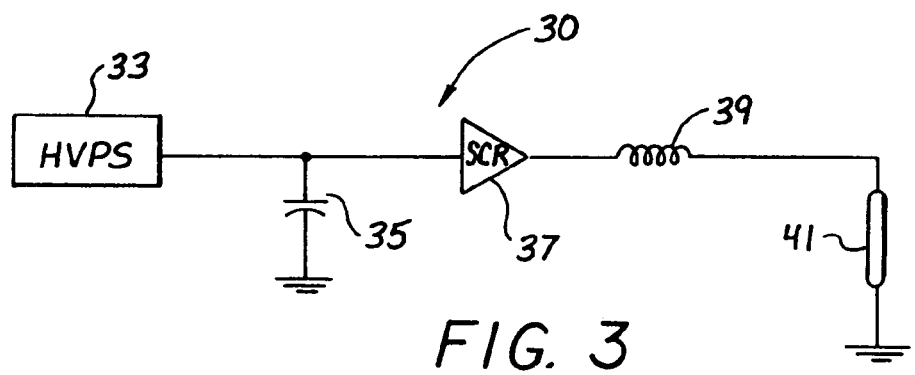
FIG. 3 is a schematic circuit diagram illustrating a circuit for generating a flashlamp-driving current in accordance with the present invention.

FIG. 3 illustrates a flashlamp-driving circuit 30 according to the presently preferred embodiment. The flashlamp-driving circuit 30 comprises a high-voltage power supply 33, a capacitor 35, a rectifier 37, an inductor 39, and a flashlamp 41. The capacitor 35 is connected between the high-voltage power supply 33 and ground, and the flashlamp 41 is connected between the inductor 39 and ground. The high-voltage power supply 33 preferably comprises a 1500 volt source, having a charging rate of 1500 Joules per second. The flashlamp 41 may comprise a 450 to 700 torr source and, preferably, comprises a 450 torr source. The capacitor 35 preferably comprises a 50 microfarad capacitor, and the rectifier 37 preferably comprises a silicon-controlled rectifier. The inductor 39 preferably comprises a 50 microhenry solid-core inductor. In alternative embodiments, the inductor 39 may comprise a 13 microhenry inductance. In still other alternative embodiments, the inductor 39 may comprise inductance values of between 10 and 15 micro-henries. Other values for the inductor 39 and the capacitance 35 may be implemented in order to obtain flashlamp-driving currents having relatively large leading amplitudes, for example, as discussed below.

Figure 4:
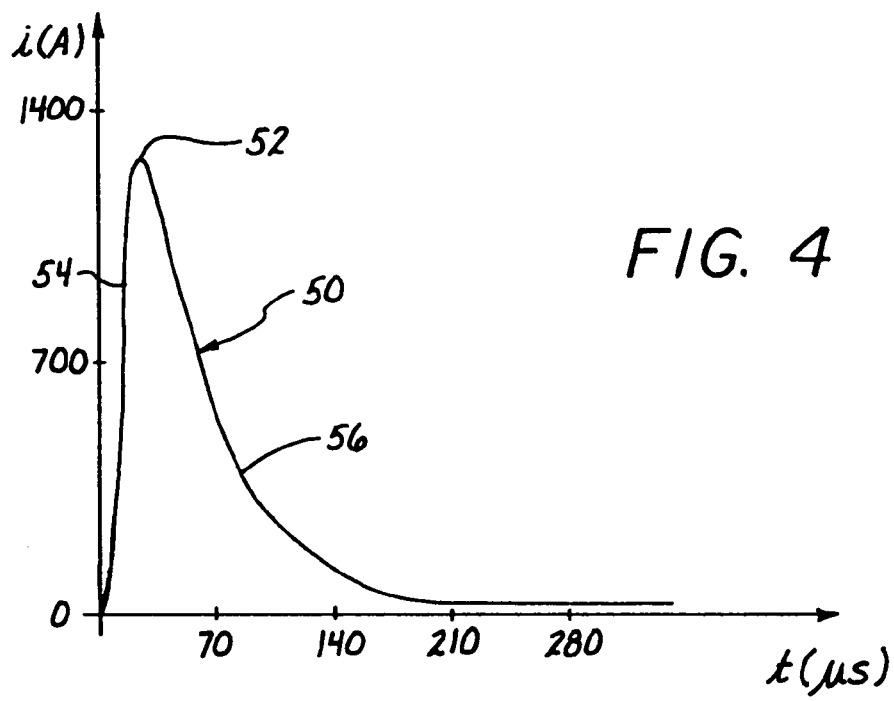
FIG. 4 is a plot of flashlamp-driving current versus time in accordance with the present invention.

FIG. 4 illustrates the flashlamp driving current 50 of the present invention, which passes from the inductor 39 to the flashlamp 41. The flashlamp driving current of the present invention preferrably has a pulse width which is greater than about 0.25 microseconds and, more preferrably, which is in a range of 100 to 300 mircoseconds. In the illustrated embodiment, the pulse width is about 200 microseconds. The flashlamp driving current 50 comprises a maximum value 52, an initial ramp portion 54, and a declining current portion 56. The flashlamp 41 preferably comprises a cylindrical glass tube having an anode, a cathode, and a gas therebetween such as Xenon or Krypton. An ionizer circuit (not shown) ionizes the gas within the flashlamp 41. As the flashlamp-driving current 50 is applied to the anode of the flashlamp 41, the potential between the anode and the cathode increases. This potential increases as the flashlamp-driving current increases, as indicated by the initial ramp 54. Current flows through the gas of the flashlamp 41, resulting in the flashlamp 41 emitting bright incoherent light.

The flashlamp 41 is close-coupled to laser rod (not shown), which preferably comprises a cylindrical crystal. The flashlamp 41 and the laser rod are positioned parallel to one another with preferably less than 1 centimeter distance therebetween. The laser rod is suspended on two plates, and is not electrically connected to the flashlamp-driving current circuit 30. Although the flashlamp 41 comprises the preferred means of stimulating the laser rod, other means are also contemplated by the present invention. Diodes, for example, may be used instead of flashlamps for the excitation source The use of diodes for generating light amplification by stimulated emission is discussed in the book Solid-State Laser Engineering, Fourth Extensively Revised and Updated Edition, by Walter Koechner, published in 1996, the contents of which are expressly incorporated herein by reference.

The incoherent light from the presently preferred flashlamp 41 impinges on the outer surface of the laser rod. As the incoherent light penetrates into the laser rod, impurities within the laser rod absorb the penetrating light and subsequently emit coherent light. The impurities may comprise erbium and chromium, and the laser rod itself may comprise a crystal such as YSGG, for example. The presently preferred laser system comprises either an Er, Cr:YSGG solid state laser, which generates electromagnetic energy having a wavelength in a range of 2.70 to 2.80 microns, or an erbium, yttrium, aluminum garnet (Er:YAG) solid state laser, which generates electromagnetic energy having a wavelength of 2.94 microns. As presently preferred, the Er, Cr:YSGG solid state laser has a wavelength of approximately 2.78 microns and the Er:YAG solid state laser has a wavelength of approximately 2.94 microns According to one alternative embodiment, the laser rod may comprises a YAG crystal, and the impurities may comprise erbium impurities. A variety of other possibilities exist, a few of which are set forth in the above-mentioned book Solid-State Laser Engineering, Fourth Extensively Revised and Updated Edition, by Walter Koechner, published in 1996, the contents of which are expressly incorporated herein by reference Other possible laser systems include an erbium, yttrium, scandium, gallium garnet (Er:YSGG) solid state laser, which generates electromagnetic energy having a wavelength in a range of 2.70 to 2.80 microns; an erbium, yttrium, aluminum garnet (Er:YAG) solid state laser, which generates electromagnetic energy having a wavelength of 2.94 microns; chromium, thulium, erbium, yttrium, aluminum garnet (CTE:YAG) solid state laser, which generates electromagnetic energy having a wavelength of 2.69 microns; erbium, yttrium orthoaluminate (Er:YAL03) solid state laser, which generates electromagnetic energy having a wavelength in a range of 2.71 to 2.86 microns; holmium, yttrium, aluminum garnet (Ho:YAG) solid state laser, which generates electromagnetic energy having a wavelength of 2.10 microns; quadrupled neodymium, yttrium, aluminum garnet (quadrupled Nd:YAG) solid state laser, which generates electromagnetic energy having a wavelength of 266 nanometers; argon fluoride (ArF) excimer laser, which generates electromagnetic energy having a wavelength of 193 nanometers; xenon chloride (XeCl) excimer laser, which generates electromagnetic energy having a wavelength of 308 nanometers; krypton fluoride (KrF) excimer laser, which generates electromagnetic energy having a wavelength of 248 nanometers; and carbon dioxide ($CO_2$), which generates electromagnetic energy having a wavelength in a range of 9 to 11 microns.

Particles, such as electrons, associated with the impurities absorb energy from the impinging incoherent radiation and rise to higher valence states. The particles that rise to metastable levels remain at this level for periods of time until, for example, energy particles of the radiation excite stimulated transitions. The stimulation of a particle in the metastable level by an energy particle results in both of the particles decaying to a ground state and an emission of twin coherent photons (particles of energy). The twin coherent photons can resonate through the laser rod between mirrors at opposing ends of the laser rod, and can stimulate other particles on the metastable level, to thereby generate subsequent twin coherent photon emissions. This process is referred to as light amplification by stimulated emission. With this process, a twin pair of coherent photons will contact two particles on the metastable level, to thereby yield four coherent photons. Subsequently, the four coherent photons will collide with other particles on the metastable level to thereby yield eight coherent photons.

The amplification effect will continue until a majority of particles, which were raised to the metastable level by the stimulating incoherent light from the flashlamp 41, have decayed back to the ground state. The decay of a majority of particles from the metastable state to the ground state results in the generation of a large number of photons, corresponding to an upwardly rising micropulse (64, for example, FIG. 5). As the particles on the ground level are again stimulated back up to the metastable state, the number of photons being emitted decreases, corresponding to a downward slope in the micropulse 64, for example The micropulse continues to decline, corresponding to a decrease in the emission of coherent photons by the laser system. The number of particles stimulated to the metastable level increases to an amount where the stimulated emissions occur at a level sufficient to increase the number of coherent photons generated. As the generation of coherent photons increases, and particles on the metastable level decay, the number of coherent photons increases, corresponding to an upwardly rising micropulse.

Figure 6:
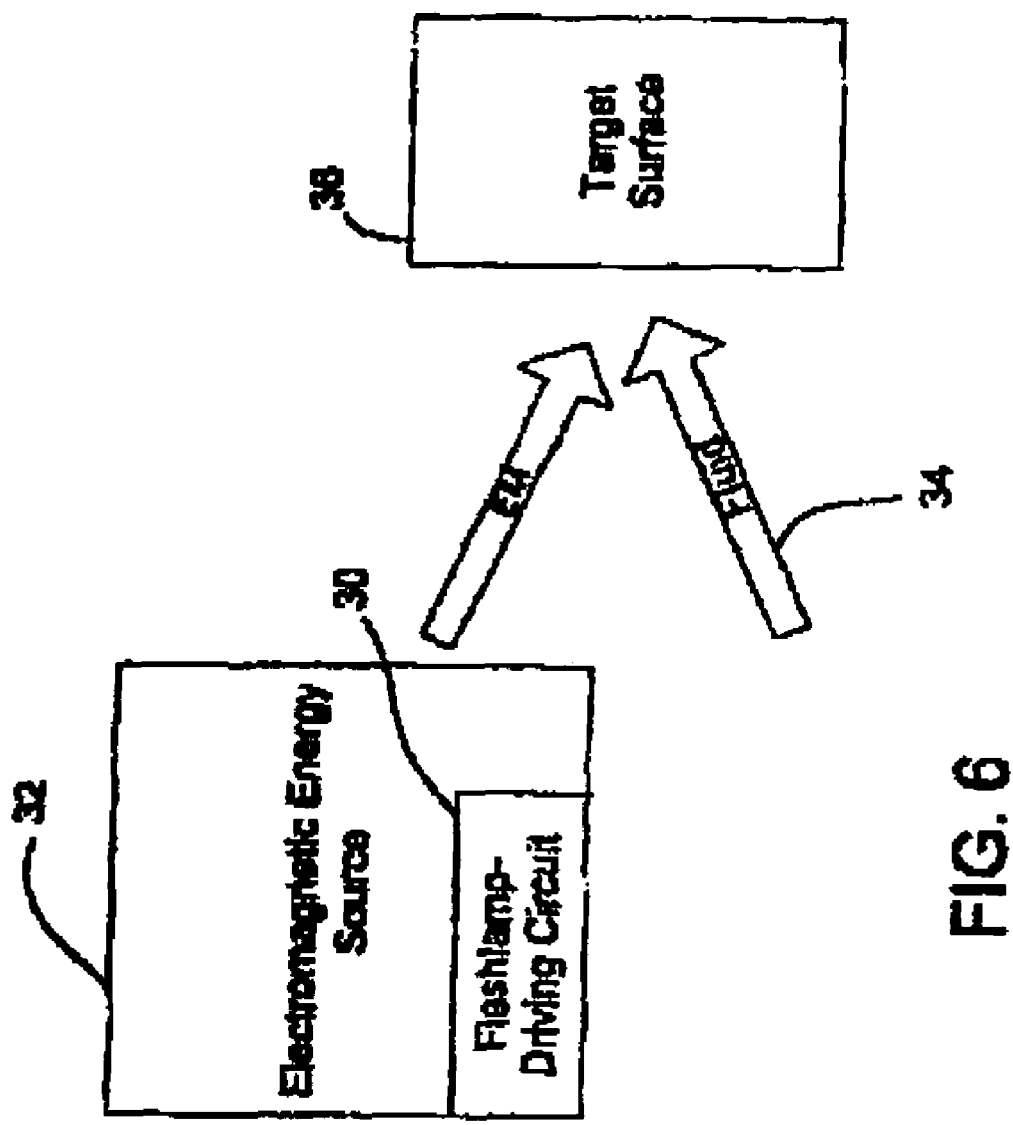
FIG. 6 is a block diagram showing a fluid output used in combination with an electromagnetic energy source having a flashlamp driving circuit in accordance with the present invention.

The output optical energy distribution 60 of the present invention is useful for maximizing a cuffing effect of an electromagnetic energy source 32, such as a laser driven by the flashlamp driving circuit 30, directed into an atomized distribution of fluid particles 34 above a target surface 36, as shown in FIG. 6. An apparatus for directing electromagnetic energy into an atomized distribution of fluid particles above a target surface is disclosed in U.S. Pat. No. 5,741,247, entitled ATOMIZED FLUID PARTICLES FOR ELECTROMAGNETICALLY INDUCED CUTTING. The high-intensity leading micropulses 64, 66, and 68 impart large amounts of energy into atomized fluid particles which preferably comprise water, to thereby expand the fluid particles and apply mechanical cutting forces to the target surface of, for example, tooth enamel, tooth dentin, tooth cementum, bone, and cartilage, skin, mucosa, gingival, muscle, heart, liver, kidney, brain, eye or vessels. The trailing micropulses after the maximum micropulse 68 have been found to further enhance the cutting efficiency. According to the present invention, a single large leading micropulse 68 may be generated or, alternatively, two or more large leading micropulses 68 (or 64, 66, for example) may be generated.

Figure 5:
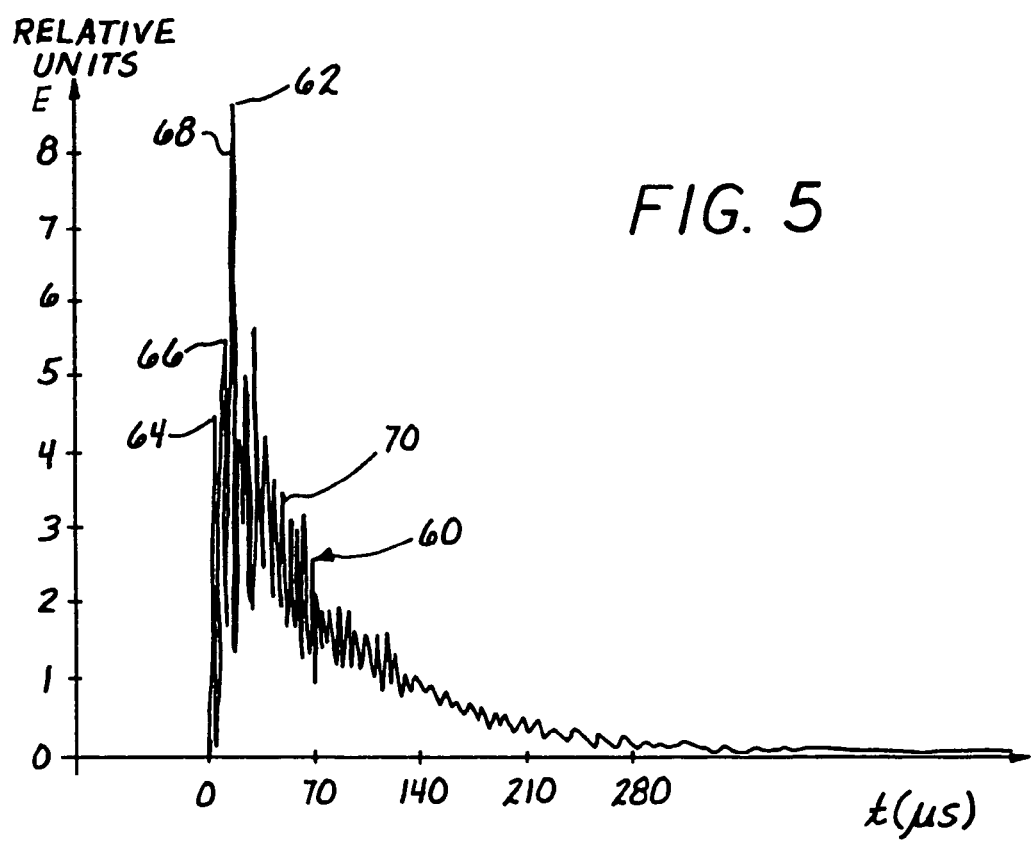
FIG. 5 is a plot of output optical energy versus time for a laser system in accordance with the present invention.

According to the present invention, the output optical energy distribution 60 comprises a large magnitude. This large magnitude corresponds to one or more sharply-rising micropulses at the leading edge of the pulse. As illustrated in FIG. 5, the micropulse 68 comprises a maximum value 62 which is at or near the very beginning of the pulse. Additionally, the full-width half-max value of the output optical energy distribution in FIG. 5 is approximately 70 microseconds, compared to full-width half-max values of the prior art typically ranging from 250 to 300 microseconds. Applicant's invention contemplates pulses comprising full-width half-max values greater than 0.025 microseconds and, preferably, ranging from 10 to 150 microseconds, but other ranges may also be possible. Additionally, Applicant's invention contemplates a pulse width of between 0.25 and 300 microseconds, for example, compared to typical prior-art pulse widths which are greater than 300 microseconds. Further, a frequency of 20 Hz is presently preferred Alternatively, a frequency of 30 Hz may be used. Applicants' invention generally contemplates frequencies between 1 and 100 Hz, compared to prior art frequencies typically ranging from 1 to 15 Hz.

As mentioned above, the full-width half-max range is defined from a beginning time, where the amplitude first rises above one-half the peak amplitude, to an ending time, where the amplitude falls below one-half the peak amplitude a final time during the pulse width. The full-width half-max value is defined as the difference between the beginning time and the ending time.

The location of the full-width half-max range along the time axis, relative to the pulse width, is closer to the beginning of the pulse than the end of the pulse. The location of the full-width half-max range is preferably within the first half of the pulse and, more preferably, is within about the first third of the pulse along the time axis. Other locations of the full-width half-max range are also possible in accordance with the present invention. The beginning time preferably occurs within the first 10 to 15 microseconds and, more preferably, occurs within the first 12.5 microseconds from the leading edge of the pulse. The beginning time, however, may occur either earlier or later within the pulse. The beginning time is preferably achieved within the first tenth of the pulse width.

Another distinguishing feature of the output optical energy distribution 70 is that the micropulses 64, 66, 68, for example, comprise approximately one-third of the maximum amplitude 62. More preferably, the leading micropulses 64, 66, 68 comprise an amplitude of approximately one-half of the maximum amplitude 62. In contrast, the leading micropulses of the prior art, as shown in FIG. 2, are relatively small in amplitude.

The slope of the output optical energy distribution 60 is greater than or equal to 5 and, more preferably, is greater than about 10. In the illustrated embodiment, the slope is about 50. In contrast, the slope of the output optical energy distribution 20 of the prior art is about 4.

The output optical energy distribution 60 of the present invention is useful for maximizing a cutting effect of an electromagnetic energy source, such as a laser, directed into an atomized distribution of fluid particles above a target surface. An apparatus for directing electromagnetic energy into an atomized distribution of fluid particles above a target surface is disclosed in co-pending U.S. application Ser. No. 08/522,503, filed Aug. 31, 1995 and entitled USER PROGRAMMABLE COMBINATION OF ATOMIZED PARTICLES FOR ELECTROMAGNETICALLY INDUCED CUTTING. The high-intensity leading micropulses 64, 66, and 68 impart large amounts of energy into atomized fluid particles which preferably comprise water, to thereby expand the fluid particles and apply mechanical cutting forces to the target surface. The trailing micropulses after the maximum micropulse 68 have been found to further enhance the cutting efficiency. According to the present invention, a single large leading micropulse 68 may be generated or, alternatively, two or more large leading micropulses 68 (or 64, 66, for example) may be generated.

The flashlamp current generating circuit 30 of the present invention generates a relatively narrow pulse, which is on the order of 0.25 to 300 microseconds, for example. Additionally, the full-width half-max value of the optical output energy distribution 60 of the present invention preferably occurs within the first 70 microseconds, for example, compared to full-width half-max values of the prior art occurring within the first 250 to 300 microseconds. The relatively quick frequency, and the relatively large initial distribution of optical energy in the leading portion of each pulse of the present invention, results in efficient mechanical cutting. If a number of pulses of the output optical energy distribution 60 were plotted, and the average power determined, this average power would be relatively low, compared to the amount of energy delivered to the laser system via the high-voltage power supply 33. In other words, the efficiency of the laser system of the present invention may be less than typical prior art systems. Since the output optical energy distributions of the present invention are uniquely adapted for imparting electromagnetic energy into atomized fluid particles over a target surface, however, the actual cutting of the present invention is optimized. The cutting effect obtained by the output optical energy distributions of the present invention is both clean and powerful and, additionally, provides a consistent cut. The terms "cut" and "cutting" are broadly defined herein as imparting disruptive mechanical forces onto the target surface.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

The invention claimed is:

1. An apparatus for imparting disruptive forces onto a target, comprising:
   a fluid output configured to place fluid into a volume in close proximity to the target; and
   an excitation source, which is configured to direct energy into the volume in close proximity to the target, wherein the excitation source outputs the energy in a form of a plurality of high-intensity leading micropulses and a full-width half-max value in a range from about 0.025 to about 250 microseconds, to impart energy into at least part of the fluid in the volume, the energy imparted into the fluid being sufficient to cause the fluid to expand wherein disruptive cutting or ablating forces are applied to the target.

2. An apparatus for imparting disruptive forces onto a target, comprising:
   a fluid output configured to place fluid into a volume in close proximity to the target; and
   an excitation source comprising a laser diode and being configured to direct electromagnetic energy into the volume in close proximity to the target, wherein the excitation source outputs at least one pulse to impart energy into at least part of the fluid in the volume, the energy imparted into the fluid being sufficient to cause the fluid to expand wherein disruptive cutting or ablating forces are applied to the target, the laser diode being configured to operate at a frequency less than about 100 Hz.

3. The apparatus as set forth in claim 2, wherein the at least one pulse is at least one output pulse.

4. The apparatus as set forth in claim 2, wherein the at least one pulse is a plurality of high-intensity leading micropulses.

5. The apparatus as set forth in any one of claims 2-4, wherein the excitation source is configured to impart energy into the fluid in the volume to thereby expand the fluid and impart the disruptive forces onto the target.

6. The apparatus as set forth in any one of claims 1 and 2-4, wherein the fluid is water.

7. The apparatus as set forth in any one of claims 1 and 2-4, wherein the excitation source comprises a diode.

8. The apparatus as set forth in any one of claims 1 and 2-4, wherein the excitation source comprises one of an Er:YAG, an Er:YSGG, an Er,Cr:YSGG, a CTE:YAG, and an Er:YALO3 laser.

9. The apparatus as set forth in any one of claims 1 and 2-4, wherein the excitation source comprises a wavelength within a range from about 2.7 to about 2.8 microns.

10. The apparatus as set forth in any one of claims 1 and 2-4, wherein the excitation source comprises a wavelength within a range from about 2.71 to about 2.86 microns.

11. The apparatus as set forth in any one of claims 1 and 2-4, wherein the target surface comprises one or more of bone, teeth, cartilage and soft tissue.

12. The apparatus as set forth in claim 11, wherein the soft tissue comprises skin.

13. An apparatus for imparting disruptive forces to a target, comprising:
    an excitation source configured to facilitate generation of at least one output pulse having a full-width half-max range closer to a beginning than an end of the output pulse; and
    a fluid output configured to direct fluid for interaction with the output pulse wherein disruptive forces are imparted to the target.

14. The apparatus as set forth in any one of claims 1, 2 and 13, wherein the apparatus comprises a plurality of fluid outputs.

15. The apparatus as set forth in any one of claims 1, 2 and 13, wherein the apparatus comprises a plurality of fluid outputs and the fluid outputs comprise nozzles.

16. The apparatus as set forth in any one of claims 1, 2 and 13, wherein the apparatus comprises a plurality of fluid outputs and the fluid outputs comprise atomizers.

* * * * *